(12) United States Patent
Jain (10) Patent No.: US 11,298,394 B1
(45) Date of Patent: Apr. 12, 2022

(54) SUPPLEMENT, DELIVERY METHOD AND DEVICE FOR SAID SUPPLEMENT

(71) Applicant: Ashoo Jain, Red Bank, NJ (US)

(72) Inventor: Ashoo Jain, Red Bank, NJ (US)

( * ) Notice: Subject to any disclaimer, the term of this patent is extended or adjusted under 35 U.S.C. 154(b) by 518 days.

(21) Appl. No.: 16/053,963

(22) Filed: Aug. 3, 2018

Related U.S. Application Data (60) Provisional application No. 62/541,515, filed on Aug. 4, 2017.

(51) Int. Cl.
*A61K 36/82* (2006.01)
*A61K 31/522* (2006.01)
*A61K 31/525* (2006.01)
*A61K 9/00* (2006.01)

(52) U.S. Cl.
CPC ............ *A61K 36/82* (2013.01); *A61K 31/522* (2013.01); *A61K 31/525* (2013.01); *A61K 9/0073* (2013.01)

(58) Field of Classification Search
None
See application file for complete search history.

(56) References Cited

U.S. PATENT DOCUMENTS

| | | | | |
|---|---|---|---|---|
| 6,576,272 B1 * | 6/2003 | Blechman | ............ | A61K 31/522 424/730 |
| 2002/0168428 A1 * | 11/2002 | Almada | ............... | A61K 36/752 424/727 |
| 2006/0134300 A1 * | 6/2006 | Newman | .................. | A23F 5/243 426/590 |
| 2007/0128327 A1 * | 6/2007 | Takashima | .............. | A23F 3/385 426/597 |
| 2015/0004282 A1 * | 1/2015 | Mills | ......................... | A23L 2/02 426/72 |

OTHER PUBLICATIONS

Brown et al., Calculating the optimum temperature for serving hotbeverages, 2008, Burns, 34: 648-654.*
Mayoclinic, 2015, https://web.archive.org/web/20150303102101/https://www.mayoclinic.org/healthy-lifestyle/nutrition-and-healthy-eating/in-depth/caffeine/art-20049372?p=1.*

* cited by examiner

*Primary Examiner* — Terry A McKelvey
*Assistant Examiner* — Catheryne Chen
(74) *Attorney, Agent, or Firm* — Nath, Goldberg & Meyer; Joshua B. Goldberg (57) ABSTRACT

A supplement formulation including a combination of vitamins, minerals, amino acids, and stimulants, and a delivery method and device for said supplement formulation. Caffeine is present in the supplement formulation in an amount of about 40-60 mg/ml, of which about 15-30 mg/ml is caffeine from coffee beans and about 15-30 mg/ml is caffeine from green tea extract. About 5-20 mg/ml caffeine from guarana seed extract may also be present. Such a delivery device provides the supplement to a mouth/throat area of a user where it is readily absorbed in the mouth/throat area of the user or ingested by the user.

9 Claims, 4 Drawing Sheets

SUPPLEMENT, DELIVERY METHOD AND DEVICE FOR SAID SUPPLEMENT

CROSS-REFERENCE TO RELATED APPLICATIONS

The present application claims priority to U.S. Provisional Patent Application No. 62/541,515, filed on Aug. 4, 2017, the contents of which are incorporated herein by reference in the entirety.

FIELD OF THE SUBJECT MATTER

This subject matter relates generally to supplement formulations, methods and delivery devices for said supplement formulations which may include a combination of vitamins, minerals, stimulants and nutraceuticals, and particularly to supplement formulations comprising a high concentration of caffeine. The delivery devices may provide the supplement formulation to a mouth/throat area of a user.

BACKGROUND

A dietary supplement, or "supplement", is intended to provide nutrients that may otherwise not be consumed in sufficient quantities. Supplements generally include vitamins, minerals, fiber, fatty acids or amino acids, among other substances. More than half of the U.S. adult population consumes some form of supplement, most commonly multivitamins or caffeine.

Caffeine and other stimulants, in moderate doses, may elevate neural activity in many parts of the brain, postpone fatigue and enhance performance of simple intellectual tasks and physical work that involves endurance. The most common therapeutic use of stimulants is to relieve pain, especially headache pain.

Typically, various pharmaceutical compositions are administered either orally or intravenously. Intravenous injection, while rapidly delivering the drug, involves discomfort and risk of infection associated with catheterization or injection. Further, intravenous delivery is often not feasible for everyday and on-the-go usage.

Conventional oral delivery of pharmaceutically active agents has long existed in the medical community with the use of solids in pill form, or liquids in spray form. Spray form can more broadly include oral sprays—which deliver active agents in a form to be ingested or buccally absorbed—or inhalers—which deliver the active agents in a form to be absorbed by the lungs. Manufacturers of supplemental spray product Vitasprays® state on their website "New evidence suggests that oral B12 works as well as injections, if not better, according to a study published in the authoritative journal 'Blood'." (Vitaspray) Present FIG. 6, taken from the same website, shows how nutrients are absorbed into the body.

Among oral delivery systems, inhalers and other similar oral delivery systems have problems of delivering inaccurate doses, requiring frequent drug administration and/or resulting in inconsistent dosing. Further, certain precautions must be made when introducing a substance to a subject's lungs, as opposed to a subject's mouth and/or throat area. For example, effective and efficient formulation for delivery via an inhaler presents significant challenges. To deliver agents via inhalation, compounds or mixtures must be precisely formulated to ensure that they are deposited to the appropriate part of the lung and to deliver a correct amount of agent over an appropriate period of time. Meeting these objectives requires control of key factors such as particle size and density and compatibility with select delivery devices.

Various systems and methodologies for delivering supplements are known in the art. However, their structure and means of operation fail to solve all the problems discussed above.

U.S. Pat. No. 9,308,208 pertains to a method and device to generate an aerosol having a desired particle size, i.e., from molecular to about 10 microns, which can be used to effectively deliver a physiologically active compound to organs and tissues such as the lung, eye, mucosa and skin. The aerosol is formed through vaporization of the compound while mixing the resulting vapor with a gas, in a ratio, to form the desired particle size when a stable concentration of particles in the gas is reached.

U.S. Pat. No. 7,488,469 pertains to delivery of caffeine through an inhalation route. Specifically, it relates to aerosols containing caffeine used in inhalation therapy. The aerosol includes particles comprising at least 5 percent by weight/volume (% w/v) of caffeine. Caffeine is delivered to a mammal through an inhalation route. The method includes: a) heating a composition, wherein the composition includes at least 5% w/v caffeine, to form a vapor; and b) allowing the vapor to cool, thereby forming a condensation aerosol comprising particles, which is inhaled by the mammal. A kit for delivering caffeine through an inhalation route to a mammal is provided which includes: a) a composition comprising at least 5% w/v caffeine; and b) a device that forms a caffeine containing aerosol from the composition to be inhaled by the mammal.

U.S. Patent Application Publication No. 2016/0151275 pertains to an aerosolized formulation for use in a metered dose inhaler. The disclosed formulation includes at least one active ingredient, at least one solvent and at least one propellant. None of the at least one active ingredient, the at least one solvent and the at least one propellant include water.

The above examples of existing technology fail to meet one or more of the following objectives:

- Provide a method and delivery device that delivers a metered dose of a supplement to a user.
- Provide a delivery device that is lightweight and easy to use.
- Provide a delivery device that is readily portable.
- Provide a delivery device that allows for oral absorption of the supplement.
- Provide a delivery device that delivers amino acids to a user.
- Provide a delivery device that delivers a blend of the supplement and other nutrients for a biologically relevant purpose, i.e., nutraceutical.
- Provide a delivery device that delivers stimulants.
- Provide a delivery device that has multiple use application.

Embodiments of the present subject matter provide a delivery device that delivers at least one of caffeine, vitamins and minerals to a user by a structure and means of operation which, as described below, are substantially different from existing systems and methods, enabling the embodiments to meet and exceed the above objectives.

BRIEF SUMMARY

The present subject matter and its embodiments provide for a supplement formulation and a delivery device for said supplement formulation configured to emit a spray to be applied to a mouth/throat area of a user. The supplement(s) and the exact formulation delivered may vary but preferably include at least caffeine or another stimulant. As such, the embodiments of the present subject matter can provide a safe and effective way to gain energy quickly. For example, traditional energy-providing drinks, sprays, patches and the like require multiple applications or sprays per serving, as appropriate, to achieve the desired effects. This arises from an ineffective delivery of the active ingredient, and results in undesirable modes of usage. In contrast, the embodiments described herein provide a solution in which a user may provide about 40 mg to about 60 mg of caffeine (or other stimulant(s)) per serving through a single spray, as opposed to traditional sprays, which contain only about 12 mg to about 25 mg of caffeine via application of several sprays (see Table 1.).

The delivery device may be designed to be sleek and stylish and spray the supplement formulation directly to a mouth of a user for quick absorption, rather than for absorption in the lungs through inhalation. The delivery device can accommodate storage and administration of multiple doses, which allows the supplement formulation provided by the delivery device to function as an efficient and convenient substitute source of energy, ultimately costing less money and time than coffee and energy drinks.

Embodiments of the present subject matter may provide a metered dose that gives moderate levels of energy, rather than a jolt of high energy followed by an undesirable energetic low. In one intended usage, the user utilizes the device throughout the day to maintain an elevated level of awareness, focus and energy, without ingesting high levels of sugars or calories. Most importantly, the spray delivery of the supplement formulation by the delivery device enables the supplement formulation to be ultra-fast acting, as well as cost effective.

In one embodiment of the present subject matter, a supplement formulation comprises caffeine, and optionally, vitamin B12, vitamin B3, vitamin B6, taurine and Guarana seed extract.

In another embodiment of the present subject matter, a supplement delivery device has a housing with a first end and a second end; an opening disposed at the first end of the housing; and a canister in fluid connection with the opening, wherein the canister contains a supplement mixture; and wherein the supplement delivery device is configured to provide a metered dose of a supplement formulation by means of an oral spray.

In another embodiment of the present subject matter, a supplement delivery device comprises a housing with a first section, a second section, a first end and a second end, wherein the first section is rotatably coupled to the second section to form a cavity between the first section and the second section. An opening is disposed at the first end of the housing, wherein the opening has a flow grate disposed over a portion thereof. A canister is configured to reside in the cavity and be in fluid connection with the opening, wherein the canister contains a supplement mixture containing at least caffeine. The supplement delivery device is configured to provide a metered dose of a supplement formulation in the form of a supplement spray, wherein the supplement spray contains particles of a size configured to impact a mouth and throat of a user and thus be absorbed through oral administration.

In yet another embodiment of the present subject matter, a supplement delivery device has a housing with a first section, a second section, a first end and a second end, wherein the first section is rotatably coupled to the second section, forming a cavity therein. An opening is disposed at the first end of the housing, wherein the opening has a flow grate disposed over a portion thereof. The delivery device can further comprise a canister configured to reside in the cavity and be in fluid connection with the opening, wherein the canister contains a supplement mixture containing at least caffeine. The supplement delivery device is configured to provide a metered dose of about 0.4 ml to about 1.0 ml of a supplement formulation in the form of a supplement spray; wherein the supplement spray contains a particle size greater than 10 μm.

In one embodiment, the present subject matter provides a supplement formulation including: about 40-60 mg/ml of caffeine, and of which about 15-30 mg/ml is caffeine from coffee beans and about 15-30 mg/ml is caffeine from green tea extract. In another embodiment, the supplement formulation includes about 40-60 mg/ml of caffeine, of which about 15-25 mg/ml is caffeine from coffee beans, about 15-25 mg/ml is caffeine from green tea extract, and about 5-20 mg/ml is caffeine from guarana seed extract.

In another embodiment, the present subject matter provides a supplement formulation including: about 40-60 mg/ml of caffeine, of which about 15-30 mg/ml is caffeine from coffee beans and about 15-30 mg/ml is caffeine from green tea extract; about 20-50 μg/ml of vitamin B12; about 15-20 μg/ml of vitamin B3; up to 1 μg/ml of vitamin B6; up to 10 g/ml of taurine; and about 100 mg/ml of Guarana seed extract. In a further embodiment, the present subject matter provides a supplement formulation including: about 40-60 mg/ml of caffeine, of which about 15-25 mg/ml is caffeine from coffee beans, about 15-25 mg/ml is caffeine from green tea extract, and about 5-20 mg/ml is caffeine from guarana seed extract; about 20-50 μg/ml of vitamin B12; about 15-20 μg/ml of vitamin B3; up to 1 μg/ml of vitamin B6; up to 10 g/ml of taurine; and about 100 mg/ml of Guarana seed extract.

In one embodiment, the supplement formulation has a pH of about 3-4. In another embodiment, the supplement formulation has a density of about 8 pounds per gallon.

In another embodiment, the present subject matter provides a method of formulating a supplement formulation including steps of: heating water or other appropriate solvent, adding caffeine from two or more sources in desired concentrations, and then blending the caffeine in solution with additional supplements and additives.

In another embodiment, the present subject matter provides a method of delivery of a metered dose of a liquid supplement formulation to a mouth or throat area of a user, the supplement formulation comprising about 40-60 mg/ml of caffeine, the method including: providing the caffeine in the supplement formulation, wherein the caffeine is about 15-25 mg/ml of caffeine from coffee beans, about 15-25 mg/ml of caffeine from green tea extract, and about 5-20 mg/ml of caffeine from guarana seed extract, such that the supplement mixture is stable in liquid form; and spraying, by a sprayer, a predetermined amount of 0.4-0.7 ml of the supplement mixture per spray to the mouth or throat area of the user.

In a further embodiment, the present subject matter provides a method of delivery of a metered dose of a liquid supplement formulation to a mouth or throat area of a user, the supplement formulation comprising about 40-60 mg/ml of caffeine, the method including: providing the caffeine in the supplement formulation, wherein the caffeine is about 15-30 mg/ml of caffeine from coffee beans and about 15-30 mg/ml of caffeine from green tea extract, such that the supplement mixture is stable in liquid form; and spraying, by a sprayer, a predetermined amount of 0.4-0.7 ml of the supplement mixture per spray to the mouth or throat area of the user.

In some embodiments, the sprayer is configured to produce the spray of the supplement formulation having a particle size greater than 5 μm. In other embodiments the sprayer is configured to produce the spray of the supplement formulation having a particle size greater than 10 μm.

DETAILED DESCRIPTION OF THE PREFERRED EMBODIMENTS

Figure 1:
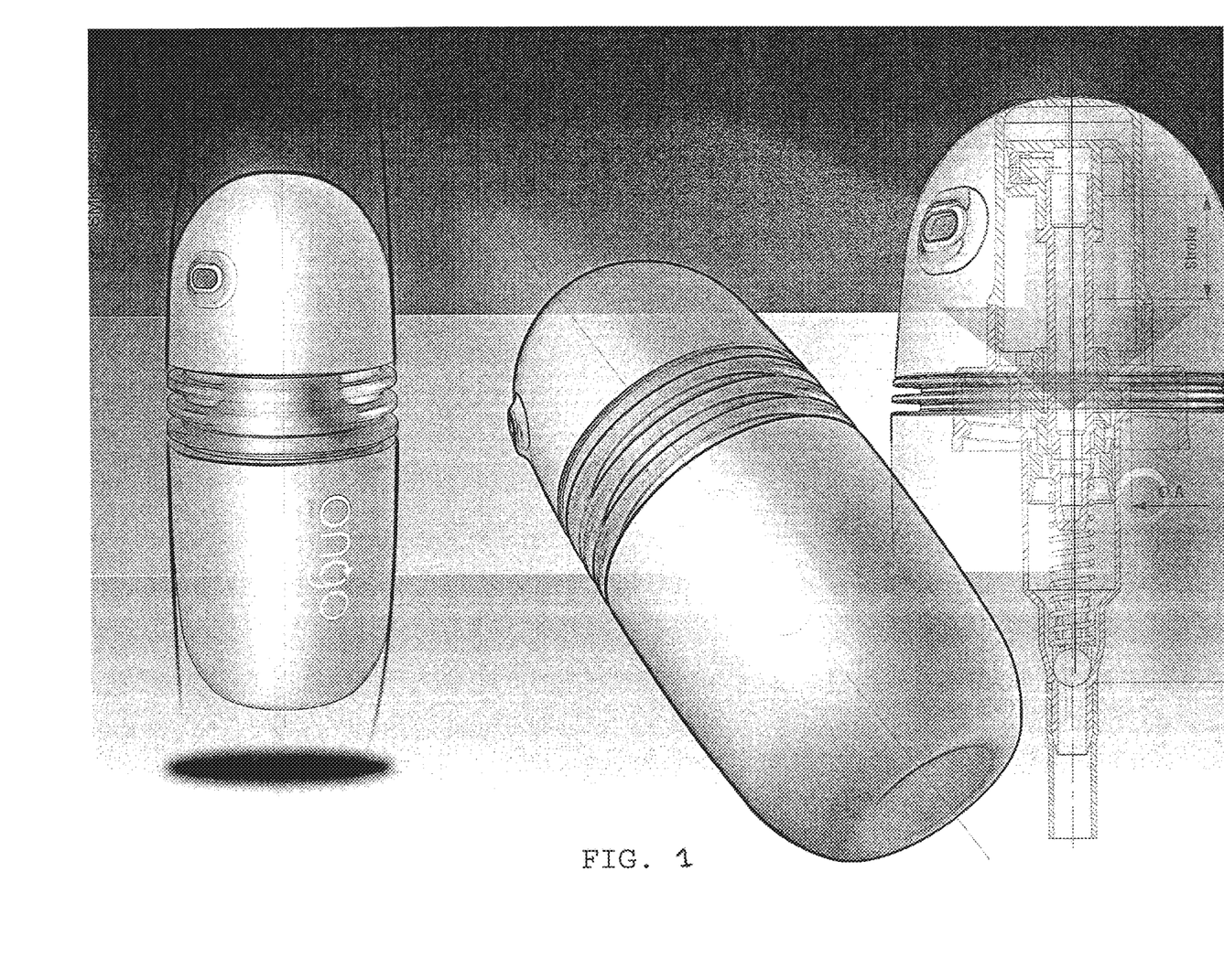
FIG. 1 shows a sprayer according to an embodiment of the present subject matter.
Figure 2:
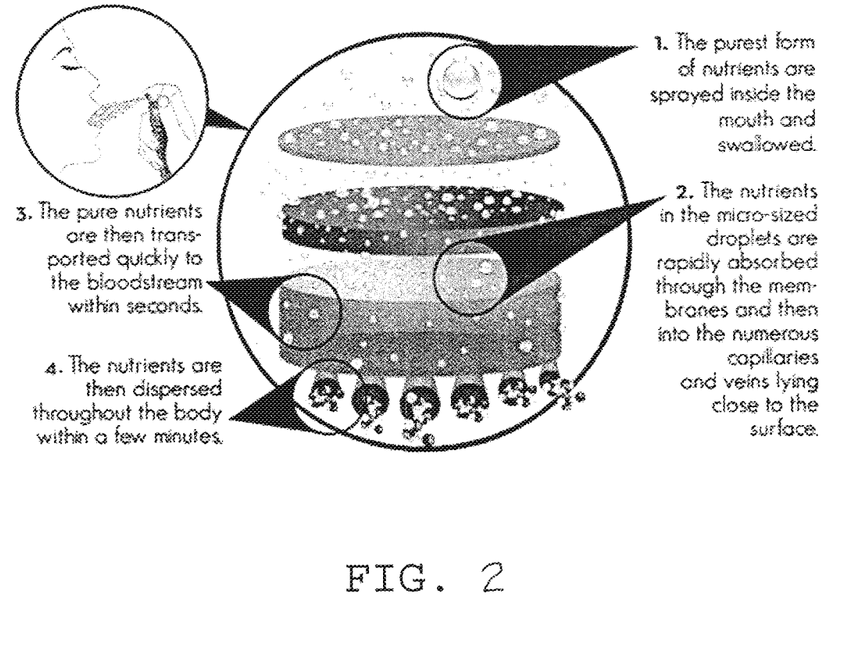
FIG. 2 shows the mechanism of oral absorption of nutrients provided by embodiments of the present subject matter.
Figure 3A:
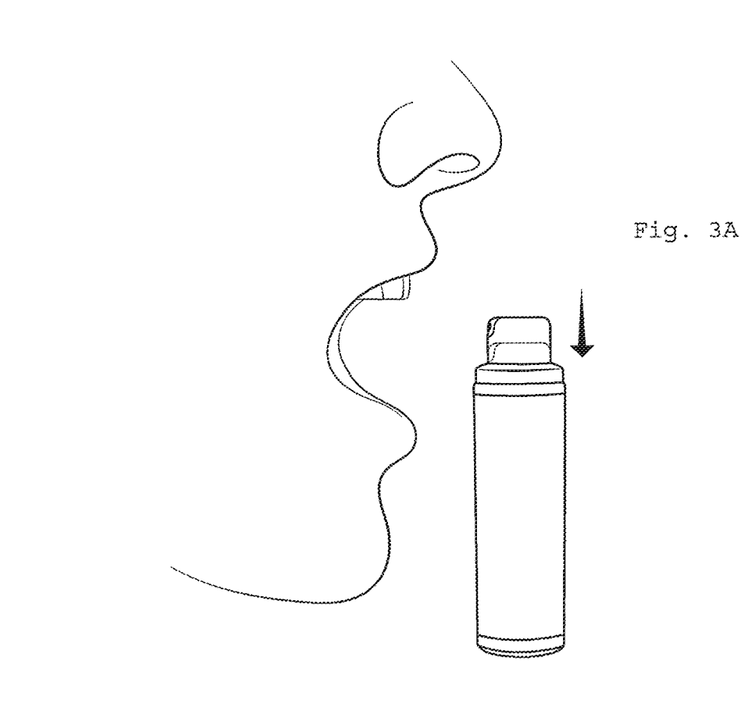
FIGS. 3A and 3B shows the mechanism for delivery of the supplement formulation from the delivery device according to certain embodiments of the present subject matter.
Figure 3B:
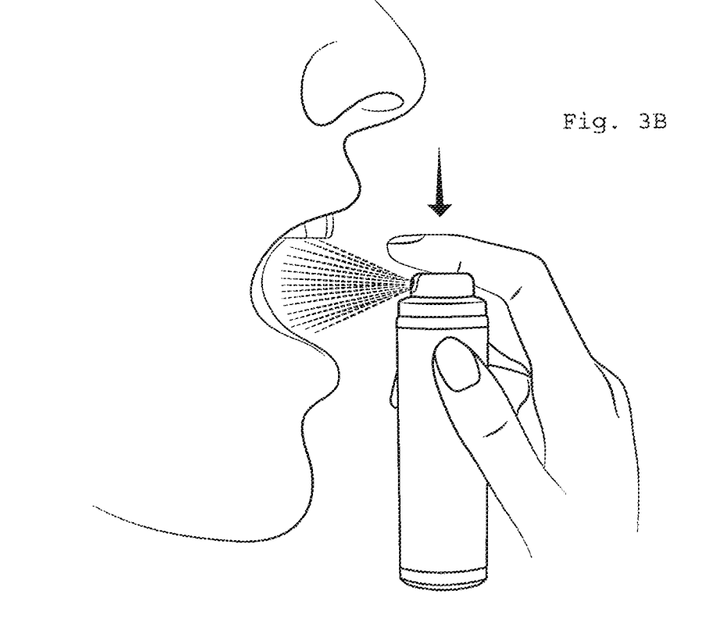

The description of illustrative embodiments according to principles of the present subject matter is intended to be read in connection with the accompanying drawings, which are to be considered part of the entire written description. In the description of embodiments of the subject matter disclosed herein, any reference to direction or orientation is merely intended for convenience of description and is not intended in any way to limit the scope of the present subject matter. Relative terms such as "lower," "upper," "horizontal," "vertical," "above," "below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated as such. Terms such as "attached," "affixed," "connected," "coupled," "interconnected" and similar refer to a relationship wherein structures are secured or attached to one another either directly or indirectly through intervening structures, as well as both movable or rigid attachments or relationships, unless expressly described otherwise. Moreover, the features and benefits of the subject matter are illustrated by reference to the exemplified embodiments. Accordingly, the subject matter expressly should not be limited to such exemplary embodiments illustrating some possible non-limiting combination of features that may exist alone or in other combinations of features; the scope of the subject matter being defined by the claims appended hereto.

This disclosure describes the best mode or modes of practicing the subject matter as presently contemplated. This description is not intended to be understood in a limiting sense, but provides an example of the subject matter presented solely for illustrative purposes by reference to the accompanying drawings to advise one of ordinary skill in the art of the advantages and construction of the subject matter. In the various views of the drawings, like reference characters designate like or similar parts.

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition, an apparatus, or a method described herein can be combined in a variety of ways without departing from the spirit and scope of the present teachings, whether explicit or implicit herein The use of the terms "include," "includes", "including," "have," "has," or "having" should be generally understood as open-ended and non-limiting unless specifically stated otherwise.

The use of the singular herein includes the plural (and vice versa) unless specifically stated otherwise.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

Reference will now be made in detail to each embodiment of the present subject matter. Such embodiments are provided by way of explanation of the present subject matter, which is not intended to be limited thereto. In fact, those of ordinary skill in the art may appreciate upon reading the present specification and viewing the present drawings that various modifications and variations can be made thereto.

In one aspect, the present subject matter relates to a portable delivery device configured to deliver a combination of stimulants, vitamins, amino acids, minerals, etc. orally. Preferably, the delivery device delivers a supplement formulation comprising a combination of caffeine, niacin (vitamin B3), vitamin B12, vitamin B6, guarana seed extract and taurine. The delivery device may further include a canister containing an amount of a supplement formulation. The supplement formulation may contain biologically active ingredients as well as additives, such as color, flavor and preservatives.

Embodiments of the present subject matter have the following differentiating factors over existing energy supplements.

A. Caffeine Content:

Table 1 summarizes energy supplement products existing on the market in comparison to the supplemental formulation and delivery device of the present subject matter. Considering, for example, Instavit Energy Spray and Marz Reboot, both have proprietary blends of multiple ingredients that include a total of 28 mg solid blend ingredients in 1 ml of solution. It is estimated that the caffeine content in 1 ml is between 15 and 20 milligrams. In contrast, an embodiment of the present subject matter is a supplement formulation having a caffeine concentration of about 40-60 mg per 1 ml, stably in liquid solution. The stability in liquid solution of the caffeine in the supplement formulation was achieved through significant testing and experimentation to optimize solubility and stability. In attempts to achieve a desired caffeine concentration of 40-60 mg caffeine per ml using any single caffeine source, 99% of caffeine precipitated as solids out of solution in a matter of days. Surprisingly, it was found that a caffeine concentration of 40-60 mg caffeine per ml could be achieved in stable solution by using multiple sources of caffeine. An embodiment of the present subject matter is to combine caffeine from at least two sources to achieve the caffeine concentration in the desired range:

i. 15-30 mg per ml of caffeine from coffee beans; and
ii. 15-30 mg per ml of caffeine from green tea extract.

In this regard, the desired range of caffeine concentration can be obtained by using 20-30 mg per ml of caffeine from coffee beans and 20-30 mg/ml of caffeine from green tea extract.

In another embodiment, the present supplement formulations have a combination of caffeine from at least three sources to achieve the caffeine concentration in the desired range:

i. 15-25 mg per ml of caffeine from coffee beans;
ii. 15-25 mg per ml of caffeine from green tea extract; and
iii. 5-20 mg per ml of caffeine from guarana seed extract.

In this regard, the desired range of caffeine concentration can be obtained by using 15-25 mg per ml of caffeine from coffee beans, 15-25 mg/ml of caffeine from green tea extract, and 5-15 mg per ml of caffeine from guarana seed extract. In another embodiment, 10-20 mg per ml of caffeine from guarana seed extract can be used.

In some alternative embodiments, the caffeine concentration can be about 30-45 mg of caffeine per ml, using a combination of caffeine from coffee beans and green tea extract, while maintaining the mixture in stable liquid form.

In addition, it is to be noted that the amounts of caffeine present in the instant formulations represent the amount of active caffeine from each source. The amounts indicated do not include amounts of non-active caffeine from each source material. Thus, for example for guarana seed extract, a higher amount of guarana seed extract in total may be used to obtain the desired amount of the active caffeine component.

Further methodological details allowing for optimal stability of the supplement formulation with a desired high caffeine concentration are as follows:

Appropriate solvent, preferably water, is heated before any active ingredients are added, preferably to a temperature of at least 140° F. Caffeine from at least two different sources are added to the water in quantities to achieve a final concentration in the heated water of 30-60 mg/ml of caffeine, and preferably from 40-60 mg/ml of caffeine. The at least two different sources are preferably selected from a group of natural caffeine sources, such as of coffee beans and green tea extract. In some embodiments, the at least two different sources of caffeine can further comprise a third caffeine source, guarana seed extract. In an embodiment, caffeine from at least all three sources of caffeine may be added to achieve a final concentration of caffeine in the range of 40-60 mg/ml.

In one embodiment, caffeine from coffee beans should be added to a concentration of 20-30 mg/ml and caffeine from green tea extract should be added to a concentration of 20-30 mg/ml. In another embodiment, caffeine from coffee beans should be added to a concentration of 15-25 mg/ml, caffeine from green tea extract should be added to a concentration of 15-25 mg/ml and caffeine from guarana seed extract should be added to a concentration of 5-20 mg/ml. In an embodiment, the caffeine from coffee beans can be from green coffee beans. Caffeine from other sources of caffeine, natural and synthetic, may additionally be added; however, synthetic caffeine anhydrous, for example, was found to be less soluble than the above listed natural caffeine sources.

After adding caffeine, the solution is blended, which blending is preferably maintained while additional ingredients are added. Additional ingredients added may be chosen from a group of biologically active ingredients including, but not limited to, vitamins and minerals, including vitamins B3, B6 and B12, Taurine and Guarana seed extract. Additional additives may be added, such as coloring agents, flavoring agents (e.g., sweeteners) and compatible solvents. In one embodiment, a pH of the supplement formulation is adjusted to a range of pH 3-4. A viscosity of the supplement formulation may be increased by addition of glycerin. Various mixtures and combinations of any of the above may be added, as appropriate.

If a preservative is to be added to the final supplement formulation, said preservative may be added before or after heating of water, but before adding caffeine.

The supplement formulation may be formulated at a large scale, for example in batches of around 50 gallons, or around 6000 units, and bottled for delivery. During formulating and bottling of the supplement formulation, the supplement formulation should be continuously agitated to maintain ingredients in solution. In one embodiment, the supplement formulation has a final density of 8 lb/gallon.

The supplement formulation made according to the method of the above embodiment may be delivered by a delivery device according to the present specification or by another appropriate delivery method, such as a dropper, measuring spoon or an existing cosmetic or pharmaceutical delivery container, e.g., cosmetic spray or pump bottle.

In comparison, typical caffeine content of prominent existing energy drinks are:

i. Red Bull: Approximately 80 mg caffeine in approximately 250 ml, equaling 0.32 mg caffeine per milliliter.

ii. 5 Hour energy: Approximately 200 mg caffeine in approximately 60 ml, equaling 3.3 mg caffeine per milliliter.

The caffeine content of the supplement formulation according to the above embodiments of the present subject matter is significantly higher on a per ml basis than relevant existing products, and importantly, by a factor of at least 2-3 times relative to the closest existing caffeinated concentrate (see Table 1).

B. Spray Volume:

Other energy sprays in the market that deliver stimulants via an oral spray form deliver insufficient caffeine content per spray for efficient and convenient effective use.

For example, Marz Reboot and Instavit each requires 4-7 sprays per serving, with a volume dispersed per spray being in the range of 0.1 ml to 0.15 ml.

For the supplement formulation formulated according to the methods of the above embodiments and delivered as an oral spray using the delivery device of the present subject matter, the oral spray can be delivered between about 0.4 ml and about 1.0 ml per spray, giving 3-7 times greater volume dispersed per spray. In some embodiments, the present oral spray can be delivered between about 0.4 ml and about 0.7 ml per spray. In other embodiments, the present oral spray can be delivered at about 0.5 ml per spray By providing the supplement formulation with improved stability of caffeine in solution allowing for greater caffeine concentration and with physical properties such that the delivery device delivers increased spray volume per spray, an embodiment of the present subject matter delivers approximately 6-20 times greater caffeine per spray than the closest relevant existing products.

Table 1 below provides a summary of comparable features of embodiments of the present subject matter over existing products:

TABLE 1

Feature comparison of existing energy supplement products

| | Red Bull | 5 Hr Energy | Marz Spray | Instavit | Gevitta | Sparx | Black Bear Spray | Present Subject Matter |
|---|---|---|---|---|---|---|---|---|
| Year Founded | 1987* | 2002 | 2014 | 2015 | 2014 | 2017 | 2017 | 2017 |
| Format: | Drink | Shot | Spray | Spray | Spray | Spray | Spray | Spray |
| Serving Size: | 8.4 oz | 1.93 oz (1 oz) | 1 ml | 0.5 ml | 0.5 ml | 0.90 grams | 0.8 ml | 1.5 ml |
| Per Unit Per Serving: | 1 serving | 2 servings | 30 servings | 28 servings | 15 servings | 33 servings | 31 Servings CAFFEINE FREE | 20 servings |
| Serving unit | 1 drink | 2 servings in 1 shot bottle | 7 sprays (1 ml) | 4 sprays | 8 sprays | 6 sprays | 5 sprays | 3 sprays |
| Caffeine | 80 mg | 200 mg - 240 mg in extra strength | Undisclosed: <28 mg blend (caffeine est. under 20) | Undisclosed <30 mg blend (caffeine est. under 20) | undisclosed | Undisclosed: <90 mg blend (caffeine est. under 30) | 0 | 75 mg |
| B3 (Niacin) | 20 mg (100%) | 30 mg (150%) | 0 | 0.5 mg (3%) | undisclosed | 0 | 2.8 mg (14%) | 24 mg (150%) |
| B6 | 4.5 mg (250%) | 40 mg (2000%) | 0.67 mg (33%) | 0 | undisclosed | 0 | 0.9 mg (45%) | 4.9 mg (288%) |
| B12 | 4 µg (80%) | 500 µg (8333%) | 0 | 50 µg (800%) | 0 | 500 µg (8000%) | 2500 µg (41,000%) | 75 µg (3125%) |
| Taurine: | unknown | Blended, high | Blended | None | undisclosed | 0 | 0 | 75 mg |
| mg of Caffeine per spray (Approximates) | N/A | N/A | 2.86 | 5 | undisclosed | 5 | 0 | 25 |
| Servings to achieve 80 mg Caffeine (Approximates) | 1 Bottle | 0.4 | 28 | 16 | undisclosed | 16 | Infinity | 3.2 |
| Caffeine per 1 ml | appx. 0.3 mg/ml | extra strength at 4.0 mg/ml | Est. under 20 mg/ml | Est. under 20 mg/ml | undisclosed entirely | Est. at 25 mg/ml | 0.00 | 50 mg/ml |

In at least one embodiment of the present subject matter, the metered dose dispensed by the delivery device is as follows:

Approximate dosage volume: 1 ml 40-60 mg of caffeine 20-50 µg of B12

15-20 µg of B3

Up to 1 µg of B6

Up to 10 g of Taurine 100 mg of Guarana seed extract

Solvent(s)

Flavoring agents

Sweetener(s)

pH of 3-4

Density of about 8 pounds per gallon

It is intended that the spray will be absorbed by, e.g., the intestinal tract. The spray can be administered frequently throughout the day on an as-needed basis. Preferably, a user will not exceed 2-3 sprays in any 4-hour period, depending on the strength and contents of the supplement mixture.

In one embodiment, the delivery device can have a housing, first end, second end, opening, canister, supplement mixture, spray mechanism/actuator, flow grate, cavity, first section and second section.

In another embodiment, the delivery device may have a receptacle and a spray cap, whereby depression of the spray cap causes a metered spray (about 0.4 ml to about 0.7 ml) of the supplement formulation to be emitted onto a surface or into the surrounding environment.

The housing may be a singular structure or consist of two or more sections. These sections join to form a cavity where the canister resides. A receptacle in the cavity may be used to join or couple the canister to the housing.

The housing can have an opening disposed in either of the first or the second end. The opening can be shaped and configured to accommodate a mouth of a user and direct the spray into the mouth of the user. A flow grate may further serve to direct the spray to the user's mouth and to prevent the passage of any larger or undesirable materials which may be caught up in the spray to not enter the mouth of the user. In some embodiments, the housing may be separated to allow for a new canister to be inserted into the device and in other embodiments allow for the removal and refilling of the canister. The canister may then be reinserted.

The canister can be in the shape of a cylinder. In some embodiments, the canister can contain about 60 sprays, or a total capacity of between about 24 ml and 42 ml. The canister can further have an actuator that, when depressed, enables the supplement mixture to be dispensed in a metered spray. The canister can further be configured to reside in a cavity of the housing as described herein.

In one embodiment, a user can hold the delivery device at a distance from the user's mouth or covers the opening of the device with the user's mouth and activate the actuator of the cylinder or canister. The supplement mixture is then released in the form of a spray. The actuator may be activated by depressing the canister or a portion of the housing of the device. In other embodiments, depressible buttons may be utilized. In one embodiment, the spray has a desired average particle size greater than 10 μm, thereby preventing the spray from passing into an airway of the user.

In an embodiment, the delivery device is shaken by the user immediately prior to spraying, thereby avoiding any possible sedimentation of the supplement formulation contained therein. This has the dual benefit of maximizing the uniformity of spray composition and avoiding any clogging of the delivery device.

C. Delivery Device Structure and Function:

Presently, existing nutraceuticals and dietary supplements delivered in a spray format utilize a standard sprayer in a standard bottle. FIG. 1 shows various views of the delivery device according to one embodiment of the present subject matter. The delivery device according to an embodiment of the present subject matter is unique at least for comprising the following three elements:

i. a bottle bottom that contains the supplement formulation;

ii. a sprayer comprising an accordion shaped element, referred to hereafter as an accordion, which is flexible and can be depressed; and iii. a bottle top that, with the bottle bottom, completely conceals a sprayer inside.

When depressed, the bottle top pushes down on the accordion and a spray hole in the bottle top moves synchronously with the sprayer head to disperse the supplement formulation. The sprayer is screwed or crimped into the bottom of the bottle; the accordion is snapped into the bottom of the bottle and the bottle top is snapped into the accordion, making the bottle a single unit that does not come apart. The sprayer is concealed to the eye when the delivery device is assembled as described. This sprayer is designed or configured to deliver between 0.4 ml and 1.0 ml per spray, such that it is most suitable for delivering the supplement formulation in accordance with the present subject matter. In an embodiment, the sprayer is configured to deliver 0.5 ml per spray. Accordingly, the sprayer has a larger orifice size than is typical for a liquid supplement sprayer, to accommodate the larger amount of spray being delivered, as well as the particle size of the formulation being delivered. As such, sprayers typically used with, for example, lotions, can be used herein.

While the present subject matter has been described at some length and with some particularity with respect to the several described embodiments, it is not intended that it should be limited to any such particulars or embodiments or any particular embodiment, but it is to be construed with references to the appended claims so as to provide the broadest possible interpretation of such claims in view of the prior art and, therefore, to effectively encompass the intended scope of the subject matter. Furthermore, the foregoing describes the subject matter in terms of embodiments foreseen by the inventor for which an enabling description was available, notwithstanding that insubstantial modifications of the subject matter, not presently foreseen, may nonetheless represent equivalents thereto.

What is claimed is:

1. A method of formulating a supplement formulation comprising steps of:

1) obtaining an extract containing caffeine from coffee beans;

2) obtaining an extract containing caffeine from green tea;

3) heating water to at least 140° F.; and 4) adding the extract containing caffeine from coffee beans and the extract containing caffeine from green tea to the water;

wherein the formulation has a final concentration of caffeine between 40 and 60 mg/ml.

2. The method of claim 1, wherein the water is heated to about 160° F.

3. The method of claim 1, wherein caffeine from guarana seed extract is further added in step 4.

4. The method of claim 1, wherein no additional ingredients are added to the water before the caffeine is added, except for an optional preservative.

5. The method of claim 4, wherein additional ingredients selected from the group consisting of vitamins, minerals, flavoring agents, coloring agents, solvents, and mixtures thereof are added to the caffeine in solution under constant agitation.

6. The method of claim 1, further comprising adjusting the pH of the supplement formulation to be about 3-4.

7. The method of claim 5, further comprising adjusting the viscosity of the supplement formulation by addition of glycerin.

8. The method of claim 7, wherein the supplement formulation comprises about 15-25 mg/ml of caffeine from coffee beans, about 15-25 mg/ml of caffeine from green tea extract, and about 5-20 mg/ml of caffeine from guarana seed extract and is stable in liquid form.

9. The method of claim 7, wherein:
the supplement formulation further comprises about 20-50 µg/ml of vitamin B12, about 15-20 µg/ml of vitamin B3, up to 1 µg/ml of vitamin B6, and up to 10 g/ml of taurine.

* * * * *